United States Patent [19]
Brahmbhatt et al.

[11] Patent Number: 5,149,500
[45] Date of Patent: Sep. 22, 1992

[54] COMPACT SYSTEM FOR RECOVERY OF STERILIZING GAS MIXTURES

[75] Inventors: Sudhir R. Brahmbhatt, Macungie; George A. Timberlake, Jr., Gilbertsville, both of Pa.

[73] Assignee: MG Industries, Valley Forge, Pa.

[21] Appl. No.: 680,517

[22] Filed: Apr. 4, 1991

[51] Int. Cl.$^5$ .............................................. A61L 2/00
[52] U.S. Cl. ...................................... 422/31; 422/30; 422/34; 422/292
[58] Field of Search ...................... 422/30, 31, 34, 200, 422/292

[56] References Cited

U.S. PATENT DOCUMENTS

| | | | |
|---|---|---|---|
| 3,549,312 | 12/1970 | Ernst | 422/31 |
| 3,851,043 | 11/1974 | Gunther | 422/30 |
| 4,112,054 | 9/1978 | Feingold et al. | 423/245 |
| 4,812,292 | 3/1989 | Joslyn | 422/31 |
| 4,954,315 | 9/1990 | Brahmbhatt | 422/31 |
| 5,069,686 | 12/1991 | Baker et al. | 55/16 |

Primary Examiner—Robert J. Warden
Assistant Examiner—T. A. Trembley
Attorney, Agent, or Firm—William H. Eilberg

[57] ABSTRACT

A sterilizing gas mixture, containing ethylene oxide and a diluent, is used to sterilize articles in a sterilizing chamber. When the sterilization has been completed, the chamber is purged of sterilizing gas, usually in two or more purging cycles. During the first purging cycle, the spent sterilizing gas mixture is directed to a condenser, where the residual ethylene oxide and diluent are liquefied. During the second and subsequent purging cycles, the additional sterilizing gas mixture remaining in the chamber is conveyed to a disposal unit to dispose of the remaining ethylene oxide. The disposal unit can be a catalytic device which converts the ethylene oxide to carbon dioxide and water. Alternatively, the disposal unit can be a chemical device, such as an acid scrubber which converts the ethylene oxide into a non-toxic substance. Thus, virtually none of the ethylene oxide vents to the outside. The invention is especially suitable for use in environments where the amount of sterilizing to be done is relatively small. The invention provides an attractive return on capital investment, even for the smaller user, and generally requires less space, than comparable industrial units.

18 Claims, 2 Drawing Sheets

COMPACT SYSTEM FOR RECOVERY OF STERILIZING GAS MIXTURES

BACKGROUND OF THE INVENTION

This invention concerns the recovery of sterilizing gas mixtures, especially mixtures in which ethylene oxide is the sterilizing gas, and in which there is included a diluent gas, such as a chlorofluorocarbon.

Ethylene oxide (ETO) has long been used to sterilize articles, especially articles such as medical implements or tools. ETO is known to kill bacteria and other harmful organisms. However, ETO is now believed to be carcinogenic. Governments have imposed regulations concerning the emission of ETO into the atmosphere, and the severity and frequency of such regulations is expected to increase.

ETO is typically diluted with a relatively inert gas such as a chlorofluorocarbon. A typical diluent gas is the substance commonly known as Freon, the latter name being a trademark of DuPont. The preferred type of Freon, in the field of the present invention, is dichlorodifluoromethane ($CCl_2F_2$), which is sold under the trademark Freon-12. Throughout this application, the term "Freon" should be interpreted to include "Freon-12". Typical sterilizing gas mixtures include 88% Freon and 12% ETO.

Chlorofluorocarbons such as Freon have been suspected of harming the ozone layer in the atmosphere. For this reason, governments have also imposed limits on the emission of Freon into the atmosphere, and have imposed taxes or fees on Freon, to discourage its use and to encourage development of alternative refrigerants. Thus, the cost of Freon has increased considerably in recent years, and this trend is expected to continue.

In a typical sterilizing operation, only a portion of the ETO is consumed, the remainder being available for re-use, if it can be reclaimed. Because of the high cost of Freon, and also, more recently, because of the toxicity of ETO, various systems and methods have been devised for recovering spent sterilizing gas and re-using the Freon and/or the unconsumed ETO.

U.S. Pat. No. 4,954,315 shows a system and method for recovery of a sterilizing gas, and its disclosure is incorporated by reference herein. In the latter patent, the sterilizing gas is purged from the sterilizing chamber and conveyed to a condenser. The condenser is cooled by a cryogenic source, such as liquid nitrogen. The upper and lower sections of the condenser are separately cooled, by separate cryogenic cooling lines. The temperature in the upper section is sufficient to liquefy the ETO and Freon, but not the other gaseous impurities in the exhausted sterilizing gas mixture. The impurities are vented, while the liquefied ETO and Freon accumulate in the lower section of the condenser. Periodically, the liquefied mixture is vaporized and combined with fresh sterilizing gas mixture, to restore the desired proportion of ETO in the mixture. The reconstituted mixture can then be used in another sterilizing cycle. Alternatively, the ETO and Freon can be separated by distillation, and separately recovered for later use.

In the process described in the above-cited patent, the consumption of Freon is virtually zero, except for occasional losses due to leakage. Thus, it is seldom necessary to add Freon directly to the system. The ETO, however, is consumed during the sterilizing process, and therefore must be restored to the mixture, by adding ETO. The capital cost of the equipment used to practice the method is, in general, recoverable through the savings in the cost of the components of the sterilizing gas, especially the Freon. The major component of economic return is achieved either by re-use of the same Freon (i.e. by eliminating the need to purchase additional Freon), or by directly distilling and selling the recovered Freon. Some additional economic return can be derived through the recycling of ETO.

In the process of the cited patent, as in other ETO sterilization processes, the spent sterilizing gas is removed from the sterilizing chamber in several stages. This process is known as "purging" the chamber. The initial purging step removes most, but not all, of the sterilizing gas. Usually the first purging step removes about 90-94% of the sterilizing gas in the chamber. The second purging step may remove about 4-5%, and subsequent purging steps remove smaller amounts. Thus, it is usually necessary to purge the chamber at least two or three times, in order to remove most of the spent sterilizing gas. In all of the purging steps, there is also some air removed from the sterilizing chamber, along with the spent sterilizing gas. The least amount of air is removed during the first purging step, and greater amounts of air are removed during the subsequent purging steps. The latter statement is true because air is introduced into the chamber to accomplish the purging, and thus more air will be introduced during the second and subsequent purging steps.

Because the second and subsequent purging steps yield comparatively small amounts of sterilizing gas, it is relatively difficult, and expensive, to recover the sterilizing gas components by liquefying them. To recover a small amount of usable sterilizing gas, it is necessary to cool the relatively large amount of air that is mixed with the sterilizing gas. The latter fact is true because one must cool all of the gases conveyed into the condenser, including air. Cooling the air increases the amount of cryogenic coolant (such as nitrogen) required, and adds an expense to the system with no corresponding economic return. In practice, it is often necessary to provide a condenser capable of a large amount of heat removal, and to supply a large quantity of cryogenic coolant. The latter requires bulky storage facilities for the coolant.

While the process of the above-cited patent is extremely efficient and beneficial, it has disadvantages when used in environments where a relatively small amount of sterilization is performed each day. In a hospital or medical facility, for example, sterilization is done on a small scale. A hospital needs to sterilize medical implements and other pieces of equipment, but is not normally in the business of sterilizing vast quantities of material, as would be true for a manufacturer of medical supplies. Moreover, a hospital or medical facility may not have the facilities to store the large and bulky items of equipment necessary to practice the above-described process.

The system described in the above-cited patent is also quite expensive. The capital cost of the equipment used to practice the patented method is recoverable by the user, due to the savings generated by preserving and reclaiming the diluent gas (Freon), and/or by recycling ETO. However, in the case of a hospital or other small user, the rate at which the capital cost is recovered is unacceptably slow, simply because of the reduced throughput of sterilizing gas. The cost of the patented system can be recovered fairly quickly for large industrial users, which typically consume about 30,000–40,000 pounds of sterilizing gas mixture per month, but is recovered much more slowly in the case of a hospital, which typically uses only about 500–1000 pounds sterilizing gas mixture per month.

The present invention therefore provides an apparatus and method which enables a hospital, medical facility, or other relatively small user of sterilizing gas, to prevent the release of harmful ETO, and to recover the diluent and/or unused ETO for re-use. The system disclosed herein is sufficiently inexpensive to enable a small user to recover the capital cost reasonably quickly. It is also compact, and can be used with a small liquid nitrogen cylinder, instead of the massive liquid nitrogen storage tanks commonly used in industrial facilities.

SUMMARY OF THE INVENTION

According to the method of the present invention, a sterilizing gas including ETO and a diluent, such as Freon, is used to sterilize articles, such as medical implements, in a sterilizing chamber. After the sterilization is complete, the sterilizing chamber is then purged of spent sterilizing gas, the purging being done in several stages. During the first purging stage, the spent sterilizing gas driven from the chamber is directed to a condenser, where the gas is cooled, by cryogenic means, so that the sterilizing gas and diluent become liquefied. The liquefied gases are stored for later use. During the second and any subsequent purging stages, the sterilizing gas driven from the chamber is directed to an ETO disposal means. The disposal means may include a catalytic reactor, or catalytic destruction unit, for converting the residual ETO into carbon dioxide and water. Alternatively, the disposal means can be an acid scrubber which converts the ETO into ethylene glycol. Thus, the gas which is purged from the chamber is directed to the condenser on the first purging cycle, and to the disposal unit on the second and subsequent purging cycles. Thus, virtually all of the ETO is either condensed or converted into a non-toxic substance, such that essentially no ETO escapes into the environment.

It is therefore an object of the invention to provide an apparatus and method for performing sterilization with ethylene oxide gas.

It is another object to provide a sterilizing apparatus which is relatively inexpensive.

It is another object to provide a sterilizing apparatus which is relatively compact.

It is another object to provide an apparatus and method for sterilization, suitable for use in hospitals, other medical facilities, or other relatively small users of sterilizing equipment.

It is another object to prevent ETO from entering the environment, and to enable users of sterilizing equipment to comply with governmental regulations on emission of ETO.

It is another object to provide an apparatus which can be used effectively to treat the sterilizing gas exhausted from a sterilizing chamber.

Other objects and advantages of the invention will be apparent to those skilled in the art, from a reading of the following brief description of the drawings, the detailed description of the invention, and the appended claims.

DETAILED DESCRIPTION OF THE INVENTION

The present invention includes a system and method for sterilization of articles using sterilizing gas that includes ethylene oxide (ETO). The sterilization is typically performed with a sterilizing gas mixture which includes ETO and a diluent. The diluent is usually a chlorofluorocarbon, such as the product known by the trademark Freon, the preferred form of Freon being Freon-12. A typical composition of sterilizing gas is 12% ETO and 88% Freon, the percentages being by weight.

Figure 1:
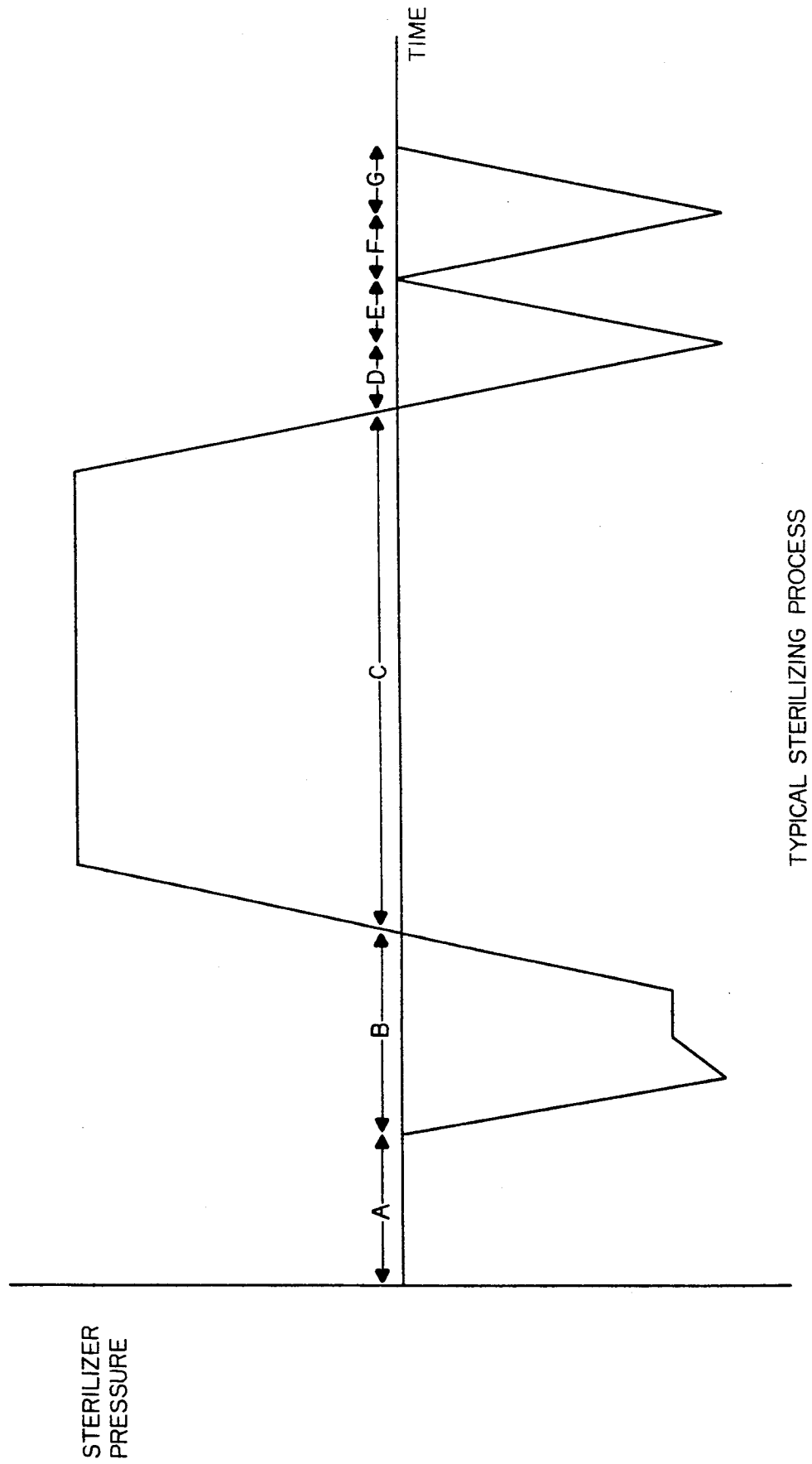
FIG. 1 is a graph illustrating the various steps in a typical sterilizing cycle.

Before explaining the present invention, it is helpful to review the steps of a typical sterilizing cycle. FIG. 1 illustrates these steps. In FIG. 1, the abscissa represents time, and the ordinate represents sterilizer pressure. The zero-point on the vertical axis (i.e. the position at which the horizontal axis is drawn) represents atmospheric pressure.

While the sterilizing chamber is still at atmospheric pressure, one places the articles to be sterilized into the chamber, and the chamber is closed. The chamber should be substantially airtight. The chamber loading step is performed in the area labeled "A" in FIG. 1.

Next, one removes the air from the chamber, creating a vacuum, and the vacuum is held for a period of time, such as about one hour. This step is represented by the area labeled "B" in FIG. 1. During this step, one may introduce steam into the chamber, which induces bacteria to come to the surfaces of the articles to be sterilized. The introduction of steam reduces the vacuum (i.e. increases the pressure in the chamber), as symbolized in FIG. 1 by a slight increase in pressure, relative to the point of minimum pressure.

While the chamber is still being held at a vacuum, the sterilizing gas mixture is injected into the chamber. The pressure in the chamber rises from a level below atmospheric (still within area "B") to a level above atmospheric pressure (area "C" of FIG. 1). When the pressure in the chamber has reached the desired level, the pressure is held constant for a period of time, typically about two hours, while the sterilization proceeds.

Then, one opens a vent line from the chamber, to allow the sterilizing gas in the chamber to escape. As the pressure in the chamber decreases towards atmospheric pressure, the vacuum pump is activated, generating another vacuum, so as to remove residual sterilizing gas from the chamber. This latter step is the first purging cycle, and is represented by area "D" of FIG. 1. When the pressure in the chamber has decreased to a preset level of vacuum, the pump is turned off, and air is allowed to flow into the chamber, and the pressure in the chamber returns to atmospheric pressure. The latter step is represented by area "E" of FIG. 1.

Then, the purging process is repeated. The pump is activated, generating another vacuum in the chamber, and causing additional residual sterilizing gas to leave the chamber (see area "F"). The pressure is raised to atmospheric pressure by pumping air into the chamber (area "G"), completing the second purging cycle. This purging process is repeated several times. Areas "F"

and "G" are similar to areas "D" and "E", respectively, and represent the second purging cycle. Additional purging cycles can be used, similar to the previous purging cycles.

During the first purging cycle, approximately 90–94% of the residual sterilizing gas mixture leaves the chamber, together with some air. On the second purging cycle, about 4–5% of the original residual sterilizing gas mixture is removed. Thus, in the first two purging cycles, approximately 94–99% of the sterilizing gas in the chamber may be removed. Subsequent purging cycles remove smaller amounts of sterilizing gas.

Figure 2:
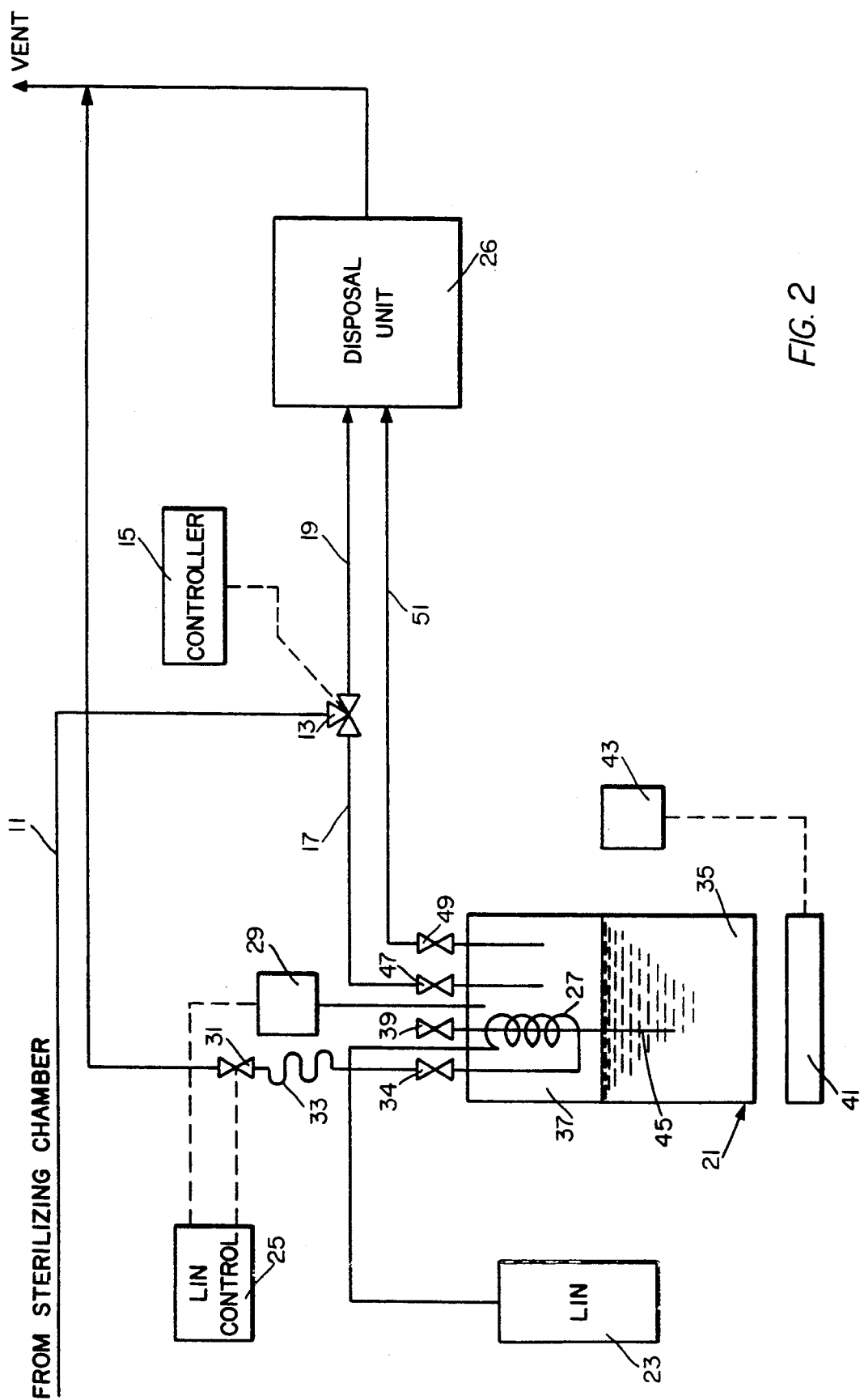
FIG. 2 is a schematic diagram of the components of the system of the present invention.

FIG. 2 is a schematic diagram of the apparatus used to practice the present invention. Conduit 11 directs the sterilizing gas mixture from a sterilizing chamber (not shown). Conduit 11 is connected to selector valve 13, which is controlled by controller 15. The controller 15 can include a relay, and also a microprocessor or other device which is programmed to change the setting of valve 13 at predetermined times.

Valve 13 is connected to direct the sterilizing gas mixture from the sterilizing chamber into either conduit 17 or conduit 19. Conduit 17 directs the gas to the cryogenic system. The main component of the cryogenic system is condenser 21. The condenser is cooled by a cryogenic liquid, such as liquid nitrogen, supplied from storage tank 23. Liquid nitrogen from the tank enters coil 27, in the condenser, and cools the gas in the head space 37 of the condenser. The sterilizing gas in the head space is thereby liquefied, and the liquid is collected at the bottom of the condenser, forming a bath 35. This liquid can later be recycled. Valve 34 is a manual valve, to facilitate disconnection of line 33, if necessary.

Nitrogen controller 25 controls the flow of liquid nitrogen from tank 23 into coil 27 of condenser 21. Controller 25 is connected to temperature sensor 29 which measures the temperature inside the condenser. When the temperature is too high, controller 25 opens valve 31, causing the gas in line 33 to vent, and thus creating a negative pressure in the coil. This negative pressure causes additional liquid nitrogen to be drawn from tank 23. Conversely, when the temperature in the condenser is sufficiently low, controller 25 closes valve 31, creating a pressure buildup in line 33 which tends to oppose the flow of liquid nitrogen out of tank 23. Valve 31 is preferably continuously variable, so that controller 25 can accurately regulate the temperature in the condenser.

Valve 39 is a manual valve used for periodically removing the accumulated liquid from the condenser. The condenser is mounted on a scale 41 which is connected to indicating device 43. When the condenser is sufficiently heavy, indicating that a large bath has accumulated, the liquid should be removed. To remove the liquid, one pressurizes the head space 37 and forces liquid through dip tube 45, and through valve 39, which can be connected to a suitable conduit (not shown).

Valve 47 is a manual valve and is used as a safety device. It makes it possible to isolate the head space from conduit 17, when necessary.

Valve 49 is also a safety device. When the system is not operating, there may be a pressure buildup in the head space, due to expansion of Freon. Valve 49 is set to open at a predetermined pressure. When the predetermined pressure is reached, valve 49 allows the gas in head space 37 to vent through line 51, into the disposal unit 26.

Conduit 19 conveys sterilizing gas from valve 13 to disposal unit 26. In one embodiment, the disposal unit is a catalytic reactor which selectively breaks down the ETO, while leaving the Freon unaffected. The disposal unit may include a heater (not shown) for accelerating the catalytic action. The reactor includes a bed of catalyst which catalyzes the desired reaction. The specific structure of the reactor used is not part of the present invention, and can be any one of several systems which are commercially available.

For example, one can use the "EO Disposer System" of the American Sterilizer Company (AMSCO), of 2424 West 23rd St., Erie, Pennsylvania. The latter system converts ETO into carbon dioxide and water vapor by catalytic combustion (flameless oxidation), with an efficiency of 99.9%. The system uses a proprietary catalyst which includes a granular material comprising manganese dioxide and copper oxide. The heater is necessary to raise the temperature of the airstream and catalyst to the catalytic reaction temperature, which is at least about 280° F. The system includes a blower which directs the sterilizing gas over the catalyst and out of the unit.

Another ETO disposal unit, similar to the unit described above, is also available from MDT Corporation, of 1777 East Henrietta Road, Rochester, New York.

Note that valve 13 may be built as part of the disposal unit, i.e. the valve can be contained within the same housing as that of the disposal unit. Alternatively, it can be a separate component, outside the disposal unit, as shown in FIG. 2.

In another embodiment, the disposal unit can be a device which uses a chemical reaction to convert ETO into a less harmful substance. For example, one can use a scrubbing system, such as is available from the Croll-Reynolds Company, Inc., under the name "ETO Scrubber No. 69282", or its substantial equivalent. This system causes the ETO gas to make intimate contact with a solution of diluted sulfuric acid. The acid absorbs the ETO gas, and is stored for a time sufficient to allow the ETO to react with the acid to form ethylene glycol. The ethylene glycol can be used for other purposes, or discarded. In either case, virtually no ETO is allowed to escape into the environment.

In operation, the sterilizing chamber is purged, as described above. On the first purging cycle, controller 15 sets valve 13 so that the purged sterilizing gas mixture flows into conduit 17, and into condenser 21. The ETO and Freon in the mixture are cooled and liquefied, and are collected at the bottom of the condenser.

Before the second purging cycle, i.e. when the next quantity of spent sterilizing gas is removed from the chamber, the controller changes the setting of the valve, so that the purged sterilizing gas enters disposal unit 26 and not condenser 21. The ETO is converted into a nontoxic substance, as described above. For the third and any subsequent purging cycles, the setting of valve 13 remains the same, and the sterilizing gas again is directed into the disposal unit. Thus, only nontoxic products will be vented from the system into the atmosphere.

The disposal units described above do not affect the Freon in the mixture, and some Freon will vent into the atmosphere. However, it turns out that the concentration of vented Freon is relatively low, usually less than 6000 parts per million, which is considered an acceptably low amount, even under the most stringent governmental regulations. The reason the amount of vented Freon is insignificant is that because Freon has a high vapor pressure, most of the Freon will be recovered during the first purging cycle, and will therefore be liquefied in the condenser. Very little additional Freon will remain in the sterilizing chamber after the first purging cycle.

While the invention has been described with respect to certain embodiments, many variations are possible. The invention is not limited to use of a particular type of disposal unit; any unit which can effectively neutralize the ETO, or convert it into a less harmful substance, can be used. The arrangement of valves can be varied considerably. The types of controllers used can be changed. For example, controller 15 can be a microprocessor, or it can be an equivalent electromechanical device. The invention is not limited to the use of a particular diluent; other diluents are possible. Other modifications to the invention can be made, and all such modifications should be deemed within the spirit and scope of the following claims.

What is claimed is:

1. A method of recovering a sterilizing gas mixture, the mixture including a sterilizing gas and a relatively inert diluent, the method being performed after completion of a sterilization operation, the method comprising the steps of:
   (a) purging a sterilizing chamber, in a first purging cycle, the purging step being the first such step performed after completion of a sterilization operation, to remove spent sterilizing gas mixture the mixture containing a sterilizing gas and a relatively inert diluent from the sterilizing chamber,
   (b) directing the spent sterilizing gas mixture from the sterilizing chamber to a means for liquefying the spent sterilizing gas mixture,
   (c) purging the sterilizing chamber, in a second purging cycle, performed after step (b), to remove residual sterilizing gas mixture from the sterilizing chamber, and
   (d) directing the residual sterilizing gas mixture obtained from step (c) into a disposal means, the disposal means comprising means for converting the sterilizing gas in the residual sterilizing gas mixture into a harmless substance.

2. The method of claim 1, further comprising the steps of repeating steps (c) and (d) at least once.

3. The method of claim 1, wherein the sterilizing gas includes ethylene oxide and wherein the relatively inert diluent includes a chlorofluorocarbon.

4. The method of claim 1 wherein the disposal means comprises a catalytic reactor.

5. The method of claim 4, wherein the sterilizing gas includes ethylene oxide and wherein the relatively inert diluent includes a chlorofluorocarbon, and wherein the catalytic reactor converts the ethylene oxide into carbon dioxide and water.

6. The method of claim 1, wherein the disposal means comprises scrubbing means for chemically converting the sterilizing gas in the residual sterilizing gas mixture into a non-toxic substance.

7. The method of claim 6, wherein the sterilizing gas includes ethylene oxide and wherein the relatively inert diluent includes a chlorofluorocarbon, and wherein the scrubbing means comprises means for reacting ethylene oxide with sulfuric acid, so as to convert the ethylene oxide into ethylene glycol.

8. Apparatus for recovery of a sterilizing gas mixture, the mixture including a sterilizing gas and a relatively inert diluent, the apparatus comprising:
   (a) a sterilizing chamber connected to a valve means,
   (b) means for directing purged sterilizing gas mixture, the mixture including a sterilizing gas and a relatively inert diluent, from the sterilizing chamber to the valve means,
   (c) the valve means comprising means for directing the purged sterilizing gas mixture into one of two conduits, the first conduit being connected to a condenser means, the condenser means comprising means for liquefying the purged sterilizing gas mixture, the second conduit being connected to a disposal means, the disposal means being distinct from the condenser means, the disposal means comprising means for converting sterilizing gas in the purged sterilizing gas mixture to a non-toxic substance, wherein the purged sterilizing gas mixture entering the condenser means does not enter the disposal means, and wherein the purged sterilizing gas mixture entering the disposal means does not enter the condenser means.

9. The apparatus of claim 8, further comprising means for controlling the position of the valve means, the controlling means being capable of connecting the diverting means either to the condenser means or to the disposal means.

10. The apparatus of claim 8, wherein the sterilizing gas is ethylene oxide, and wherein the relatively inert diluent is Freon, and wherein the disposal means comprises a catalytic reactor capable of converting the ethylene oxide into carbon dioxide and water.

11. Apparatus for recovery of a sterilizing gas mixture, the mixture including a sterilizing gas and a relatively inert diluent, the apparatus comprising:
   (a) a sterilizing chamber connected to a valve means,
   (b) means for directing purged sterilizing gas mixture, the mixture including a sterilizing gas and a relatively inert diluent, from the sterilizing chamber to the valve means,
   (c) the valve means comprising means for directing the purged sterilizing gas mixture into one of two conduits, the first conduit being connected to a condenser means, the condenser means comprising means for liquefying the purged sterilizing gas mixture, the second conduit being connected to a disposal means, the disposal means being distinct from the condenser means, the disposal means comprising means for converting sterilizing gas in the purged sterilizing gas mixture to a nontoxic substance, and
   (d) control means for controlling the position of the valve means, the control means being capable of setting the valve means to direct purged sterilizing gas mixture either into the condenser means or into the disposal means, wherein the purged sterilizing gas mixture entering the condenser means does not enter the disposal means, and wherein the purged sterilizing gas mixture entering the disposal means does not enter the condenser means.

12. The apparatus of claim 11, wherein the sterilizing gas is ethylene oxide, and wherein the disposal means comprises a catalytic reactor capable of converting the ethylene oxide into carbon dioxide and water.

13. The apparatus of claim 12, wherein the relatively inert diluent is Freon.

14. The apparatus of claim 11, wherein the sterilizing gas is ethylene oxide, and wherein the relative inert diluent is Freon, and wherein the disposal means comprises a scrubber for reacting the ethylene oxide with sulfuric acid, so as to convert the ethylene oxide into ethylene glycol.

15. Apparatus for recovery of a sterilizing gas mixture, the mixture including a sterilizing gas and a relatively inert diluent, the mixture being recovered from a sterilizing chamber, the apparatus comprising:
   (a) a sterilizing chamber connected to a valve means,
   (b) means for directing purged sterilizing as mixture, the mixture including a sterilizing gas and a relatively inert diluent, from the sterilizing chamber to the valve means,
   (c) the valve means comprising means for directing the purged sterilizing gas mixture into one of two conduits, the first conduit being connected to a condenser means, the condenser means comprising means for liquefying the purged sterilizing gas mixture, the second conduit being connected to a disposal means, the disposal means being distinct from the condenser means, the disposal means comprising means for converting sterilizing gas in the purged sterilizing gas mixture to a nontoxic substance, wherein the purged sterilizing gas mixture entering the condenser means does not enter the disposal means, and wherein the purged sterilizing gas mixture entering the disposal means does not enter the condenser means.

16. The apparatus of claim 15, further comprising means for controlling the position of the valve means, the controlling means being capable of connecting the directing means either to the condenser means or to the disposal means.

17. The apparatus of claim 15, wherein the sterilizing gas is ethylene oxide, and wherein the disposal means comprises a catalytic reactor capable of converting the ethylene oxide into carbon dioxide and water.

18. The apparatus of claim 15, wherein the sterilizing gas is ethylene oxide, and wherein the disposal means comprises a scrubber for reacting the ethylene oxide with sulfuric acid, so as to convert the ethylene oxide into ethylene glycol.

* * * * *